(12) United States Patent
Buysse et al.

(10) Patent No.: US 8,105,323 B2
(45) Date of Patent: Jan. 31, 2012

(54) METHOD AND SYSTEM FOR CONTROLLING OUTPUT OF RF MEDICAL GENERATOR

(75) Inventors: Steven P. Buysse, Longmont, CO (US); Bret S. Felton, Erie, CO (US); David N. Heard, Boulder, CO (US); David Keppel, Longmont, CO (US); Ronald J. Podhajsky, Boulder, CO (US); Dale F. Shmaltz, Fort Collins, CO (US); Robert H. Wham, Boulder, CO (US); Edward C. Meagher, Greenlawn, NY (US); Kate R. Lawes, Austin, TX (US); David A. Schechter, Longmont, CO (US); Chelsea Shields, Portland, OR (US); Philip M. Tetzlaff, Austin, TX (US); Jeremy S. James, Highlands Ranch, CO (US)

(73) Assignee: Covidien AG (CH)

( * ) Notice: Subject to any disclaimer, the term of this patent is extended or adjusted under 35 U.S.C. 154(b) by 1050 days.

(21) Appl. No.: 11/585,506

(22) Filed: Oct. 24, 2006

(65) Prior Publication Data

US 2007/0038209 A1 Feb. 15, 2007

Related U.S. Application Data

(60) Division of application No. 10/427,832, filed on May 1, 2003, now Pat. No. 7,137,980, which is a continuation-in-part of application No. 10/073,761, filed on Feb. 11, 2002, now Pat. No. 6,796,981, which is a continuation-in-part of application No. 09/408,944, filed on Sep. 30, 1999, now Pat. No. 6,398,779.

(60) Provisional application No. 60/105,417, filed on Oct. 23, 1998.

(51) Int. Cl.
*A61B 18/14* (2006.01)
(52) U.S. Cl. .............................. 606/34; 606/41
(58) Field of Classification Search .............. 606/32–35, 606/41, 42, 48–50
See application file for complete search history.

(56) References Cited

U.S. PATENT DOCUMENTS

| | | | |
|---|---|---|---|
| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |
| 1,945,867 | A | 2/1934 | Rawls |

(Continued)

FOREIGN PATENT DOCUMENTS

DE 179607 3/1905

(Continued)

OTHER PUBLICATIONS

International Search Report EP 07008207.8 dated Sep. 5, 2007.

(Continued)

*Primary Examiner* — Michael Peffley

(57) ABSTRACT

An electrosurgical generator is disclosed. The generator includes a microprocessor configured to generate a target impedance trajectory having at least one slope. The target impedance trajectory includes a plurality of target impedance values. The microprocessor is configured to drive tissue impedance along the target impedance trajectory by adjusting the output level to substantially match tissue impedance to a corresponding target impedance value. The microprocessor is further configured to compare tissue impedance to a threshold impedance value and adjust output of the electrosurgical generator when the tissue impedance is equal to or greater than the threshold impedance.

18 Claims, 4 Drawing Sheets

U.S. PATENT DOCUMENTS

| | | |
|---|---|---|
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Humio |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko et al. |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |

| Patent | Type | Date | Inventor |
|---|---|---|---|
| 4,938,761 | A | 7/1990 | Ensslin |
| 4,942,313 | A | 7/1990 | Kinzel |
| 4,959,606 | A | 9/1990 | Forge |
| 4,961,047 | A | 10/1990 | Carder |
| 4,961,435 | A | 10/1990 | Kitagawa et al. |
| 4,966,597 | A | 10/1990 | Cosman |
| 4,969,885 | A | 11/1990 | Farin |
| 4,992,719 | A | 2/1991 | Harvey |
| 4,993,430 | A | 2/1991 | Shimoyama et al. |
| 4,995,877 | A | 2/1991 | Ams et al. |
| 5,015,227 | A | 5/1991 | Broadwin et al. |
| 5,024,668 | A | 6/1991 | Peters et al. |
| 5,044,977 | A | 9/1991 | Vindigni |
| 5,067,953 | A | 11/1991 | Feucht |
| 5,075,839 | A | 12/1991 | Fisher et al. |
| 5,087,257 | A | 2/1992 | Farin et al. |
| 5,099,840 | A | 3/1992 | Goble et al. |
| 5,103,804 | A | 4/1992 | Abele et al. |
| 5,108,389 | A | 4/1992 | Cosmescu |
| 5,108,391 | A | 4/1992 | Flachenecker |
| 5,119,284 | A | 6/1992 | Fisher et al. |
| 5,122,137 | A | 6/1992 | Lennox |
| 5,133,711 | A | 7/1992 | Hagen |
| 5,151,102 | A | 9/1992 | Kamiyama et al. |
| 5,152,762 | A | 10/1992 | McElhenney |
| 5,157,603 | A | 10/1992 | Scheller et al. |
| 5,160,334 | A | 11/1992 | Billings et al. |
| 5,161,893 | A | 11/1992 | Shigezawa et al. |
| 5,167,658 | A * | 12/1992 | Ensslin .......................... 606/34 |
| 5,167,659 | A | 12/1992 | Ohtomo et al. |
| 5,190,517 | A | 3/1993 | Zieve et al. |
| 5,196,008 | A | 3/1993 | Kuenecke et al. |
| 5,196,009 | A | 3/1993 | Kirwan, Jr. |
| 5,201,900 | A | 4/1993 | Nardella |
| 5,207,691 | A | 5/1993 | Nardella |
| 5,230,623 | A | 7/1993 | Guthrie et al. |
| 5,233,515 | A | 8/1993 | Cosman |
| 5,234,427 | A | 8/1993 | Ohtomo et al. |
| 5,249,121 | A | 9/1993 | Baum et al. |
| 5,249,585 | A | 10/1993 | Turner et al. |
| 5,254,117 | A | 10/1993 | Rigby et al. |
| RE34,432 | E | 11/1993 | Bertrand |
| 5,267,994 | A | 12/1993 | Gentelia et al. |
| 5,267,997 | A | 12/1993 | Farin |
| 5,281,213 | A | 1/1994 | Milder et al. |
| 5,282,840 | A | 2/1994 | Hudrlik |
| 5,290,283 | A | 3/1994 | Suda |
| 5,295,857 | A | 3/1994 | Toly |
| 5,300,068 | A | 4/1994 | Rosar et al. |
| 5,300,070 | A | 4/1994 | Gentelia |
| 5,304,917 | A | 4/1994 | Somerville |
| 5,318,563 | A | 6/1994 | Malis et al. |
| 5,323,778 | A | 6/1994 | Kandarpa et al. |
| 5,324,283 | A | 6/1994 | Heckele |
| 5,330,518 | A | 7/1994 | Neilson et al. |
| 5,334,183 | A | 8/1994 | Wuchinich |
| 5,334,193 | A | 8/1994 | Nardella |
| 5,341,807 | A | 8/1994 | Nardella |
| 5,342,356 | A | 8/1994 | Ellman |
| 5,342,357 | A | 8/1994 | Nardella |
| 5,342,409 | A | 8/1994 | Mullett |
| 5,346,406 | A | 9/1994 | Hoffman et al. |
| 5,346,491 | A | 9/1994 | Oertli |
| 5,348,554 | A | 9/1994 | Imran et al. |
| 5,370,645 | A | 12/1994 | Klicek et al. |
| 5,370,672 | A | 12/1994 | Fowler et al. |
| 5,370,675 | A | 12/1994 | Edwards et al. |
| 5,372,596 | A | 12/1994 | Klicek et al. |
| 5,383,874 | A | 1/1995 | Jackson |
| 5,383,876 | A | 1/1995 | Nardella |
| 5,383,917 | A | 1/1995 | Desai et al. |
| 5,385,148 | A | 1/1995 | Lesh et al. |
| 5,400,267 | A | 3/1995 | Denen et al. |
| 5,403,311 | A | 4/1995 | Abele et al. |
| 5,403,312 | A | 4/1995 | Yates et al. |
| 5,409,000 | A | 4/1995 | Imran |
| 5,409,485 | A | 4/1995 | Suda |
| 5,413,573 | A | 5/1995 | Koivukangas |
| 5,414,238 | A | 5/1995 | Steigerwald et al. |
| 5,417,719 | A | 5/1995 | Hull et al. |
| 5,422,567 | A | 6/1995 | Matsunaga |
| 5,422,926 | A | 6/1995 | Smith et al. |
| 5,423,808 | A | 6/1995 | Edwards et al. |
| 5,423,809 | A | 6/1995 | Klicek |
| 5,423,810 | A | 6/1995 | Goble et al. |
| 5,423,811 | A | 6/1995 | Imran et al. |
| 5,425,704 | A | 6/1995 | Sakurai et al. |
| 5,429,596 | A | 7/1995 | Arias et al. |
| 5,430,434 | A | 7/1995 | Lederer et al. |
| 5,432,459 | A | 7/1995 | Thompson |
| 5,433,739 | A | 7/1995 | Sluijter et al. |
| 5,436,566 | A | 7/1995 | Thompson et al. |
| 5,438,302 | A | 8/1995 | Goble |
| 5,443,463 | A | 8/1995 | Stern et al. |
| 5,445,635 | A | 8/1995 | Denen et al. |
| 5,451,224 | A | 9/1995 | Goble et al. |
| 5,452,725 | A | 9/1995 | Martenson |
| 5,454,809 | A | 10/1995 | Janssen |
| 5,458,597 | A | 10/1995 | Edwards et al. |
| 5,462,521 | A | 10/1995 | Brucker et al. |
| 5,472,441 | A | 12/1995 | Edwards et al. |
| 5,472,443 | A | 12/1995 | Cordis et al. |
| 5,474,464 | A | 12/1995 | Drewnicki |
| 5,480,399 | A | 1/1996 | Hebborn |
| 5,483,952 | A | 1/1996 | Aranyi |
| 5,496,312 | A * | 3/1996 | Klicek .......................... 606/34 |
| 5,496,313 | A | 3/1996 | Gentelia et al. |
| 5,496,314 | A | 3/1996 | Eggers |
| 5,500,012 | A | 3/1996 | Brucker et al. |
| 5,500,616 | A | 3/1996 | Ochi |
| 5,511,993 | A | 4/1996 | Yamada et al. |
| 5,514,129 | A | 5/1996 | Smith |
| 5,520,684 | A | 5/1996 | Imran |
| 5,531,774 | A | 7/1996 | Schulman et al. |
| 5,534,018 | A | 7/1996 | Wahlstrand et al. |
| 5,536,267 | A | 7/1996 | Edwards et al. |
| 5,540,677 | A | 7/1996 | Sinofsky |
| 5,540,681 | A | 7/1996 | Strul et al. |
| 5,540,682 | A | 7/1996 | Gardner et al. |
| 5,540,683 | A | 7/1996 | Ichikawa |
| 5,540,684 | A | 7/1996 | Hassler, Jr. |
| 5,541,376 | A | 7/1996 | Ladtkow et al. |
| 5,545,161 | A | 8/1996 | Imran |
| 5,556,396 | A | 9/1996 | Cohen et al. |
| 5,558,671 | A * | 9/1996 | Yates .......................... 606/38 |
| 5,562,720 | A | 10/1996 | Stern et al. |
| 5,569,242 | A | 10/1996 | Lax et al. |
| 5,571,147 | A | 11/1996 | Sluijter et al. |
| 5,573,533 | A | 11/1996 | Strul |
| 5,584,830 | A | 12/1996 | Ladd et al. |
| 5,588,432 | A | 12/1996 | Crowley |
| 5,596,466 | A | 1/1997 | Ochi |
| 5,599,344 | A | 2/1997 | Paterson |
| 5,599,345 | A | 2/1997 | Edwards et al. |
| 5,599,348 | A | 2/1997 | Gentelia et al. |
| 5,605,150 | A | 2/1997 | Radons et al. |
| 5,609,560 | A | 3/1997 | Ichikawa et al. |
| 5,613,966 | A | 3/1997 | Makower et al. |
| 5,620,481 | A | 4/1997 | Desai et al. |
| 5,626,575 | A | 5/1997 | Crenner |
| 5,628,745 | A | 5/1997 | Bek |
| 5,628,771 | A | 5/1997 | Mizukawa et al. |
| 5,643,330 | A | 7/1997 | Holsheimer et al. |
| 5,647,869 | A | 7/1997 | Goble et al. |
| 5,647,871 | A | 7/1997 | Levine et al. |
| 5,651,780 | A | 7/1997 | Jackson et al. |
| 5,658,322 | A | 8/1997 | Fleming |
| 5,660,567 | A | 8/1997 | Nierlich et al. |
| 5,664,953 | A | 9/1997 | Reylek |
| 5,674,217 | A | 10/1997 | Wahlstrom et al. |
| 5,678,568 | A | 10/1997 | Uchikubo et al. |
| 5,681,307 | A | 10/1997 | McMahan |
| 5,685,840 | A | 11/1997 | Schechter et al. |
| 5,688,267 | A | 11/1997 | Panescu et al. |
| 5,693,042 | A | 12/1997 | Boiarski et al. |
| 5,693,078 | A | 12/1997 | Desai et al. |
| 5,694,304 | A | 12/1997 | Telefus et al. |
| 5,695,494 | A | 12/1997 | Becker |

| | | | | | | |
|---|---|---|---|---|---|---|
| 5,696,441 A | 12/1997 | Mak et al. | | 6,022,346 A | 2/2000 | Panescu et al. |
| 5,697,925 A | 12/1997 | Taylor | | 6,022,347 A | 2/2000 | Lindenmeier et al. |
| 5,697,927 A | 12/1997 | Imran et al. | | 6,033,399 A | 3/2000 | Gines |
| 5,702,386 A | 12/1997 | Stern et al. | | 6,039,731 A | 3/2000 | Taylor et al. |
| 5,702,429 A | 12/1997 | King | | 6,039,732 A | 3/2000 | Ichikawa et al. |
| 5,707,369 A | 1/1998 | Vaitekunas et al. | | 6,041,260 A | 3/2000 | Stern et al. |
| 5,712,772 A | 1/1998 | Telefus et al. | | 6,044,283 A | 3/2000 | Fein et al. |
| 5,713,896 A | 2/1998 | Nardella | | 6,053,910 A | 4/2000 | Fleenor |
| 5,718,246 A | 2/1998 | Vona | | 6,053,912 A | 4/2000 | Panescu et al. |
| 5,720,742 A | 2/1998 | Zacharias | | 6,055,458 A | 4/2000 | Cochran et al. |
| 5,720,744 A | 2/1998 | Eggleston et al. | | 6,056,745 A | 5/2000 | Panescu et al. |
| 5,722,975 A | 3/1998 | Edwards et al. | | 6,056,746 A | 5/2000 | Goble et al. |
| 5,729,448 A | 3/1998 | Haynie et al. | | 6,059,781 A | 5/2000 | Yamanashi et al. |
| 5,733,281 A | 3/1998 | Nardella | | 6,063,075 A | 5/2000 | Mihori |
| 5,735,846 A | 4/1998 | Panescu et al. | | 6,063,078 A | 5/2000 | Wittkampf |
| 5,738,683 A | 4/1998 | Osypka | | 6,066,137 A | 5/2000 | Greep |
| 5,743,900 A | 4/1998 | Hara | | 6,068,627 A | 5/2000 | Orszulak et al. |
| 5,743,903 A | 4/1998 | Stern et al. | | 6,074,089 A | 6/2000 | Hollander et al. |
| 5,749,869 A | 5/1998 | Lindenmeier et al. | | 6,074,386 A | 6/2000 | Goble et al. |
| 5,749,871 A | 5/1998 | Hood et al. | | 6,074,388 A | 6/2000 | Tockweiler et al. |
| 5,755,715 A | 5/1998 | Stern | | 6,080,149 A | 6/2000 | Huang et al. |
| 5,766,153 A | 6/1998 | Eggers et al. | | 6,088,614 A | 7/2000 | Swanson |
| 5,766,165 A | 6/1998 | Gentelia et al. | | 6,093,186 A | 7/2000 | Goble |
| 5,769,847 A | 6/1998 | Panescu | | 6,102,497 A | 8/2000 | Ehr et al. |
| 5,772,659 A | 6/1998 | Becker et al. | | 6,102,907 A | 8/2000 | Smethers et al. |
| 5,788,688 A | 8/1998 | Bauer et al. | | 6,113,591 A | 9/2000 | Whayne et al. |
| 5,792,138 A | 8/1998 | Shipp | | 6,113,592 A | 9/2000 | Taylor |
| 5,797,902 A | 8/1998 | Netherly | | 6,113,593 A | 9/2000 | Tu et al. |
| 5,807,253 A | 9/1998 | Dumoulin et al. | | 6,113,596 A | 9/2000 | Hooven |
| 5,810,804 A | 9/1998 | Gough et al. | | 6,123,701 A | 9/2000 | Nezhat |
| 5,814,092 A | 9/1998 | King | | 6,123,702 A | 9/2000 | Swanson et al. |
| 5,817,091 A | 10/1998 | Nardella et al. | | 6,132,429 A | 10/2000 | Baker |
| 5,817,093 A | 10/1998 | Williamson, IV et al. | | 6,142,992 A | 11/2000 | Cheng et al. |
| 5,820,568 A | 10/1998 | Willis | | 6,155,975 A | 12/2000 | Urich et al. |
| 5,827,271 A * | 10/1998 | Buysse et al. .................... 606/40 | | 6,162,184 A | 12/2000 | Swanson et al. |
| 5,830,212 A | 11/1998 | Cartmell | | 6,162,217 A | 12/2000 | Kannenberg et al. |
| 5,836,909 A | 11/1998 | Cosmescu | | 6,165,169 A | 12/2000 | Panescu et al. |
| 5,836,943 A | 11/1998 | Miller, III | | 6,171,304 B1 | 1/2001 | Netherly et al. |
| 5,836,990 A | 11/1998 | Li | | 6,183,468 B1 * | 2/2001 | Swanson et al. ................ 606/40 |
| 5,843,019 A | 12/1998 | Eggers et al. | | 6,186,147 B1 | 2/2001 | Cobb |
| 5,843,075 A | 12/1998 | Taylor | | 6,188,211 B1 | 2/2001 | Rincon-Mora et al. |
| 5,846,236 A | 12/1998 | Lindenmeier et al. | | 6,193,713 B1 | 2/2001 | Geistert et al. |
| 5,849,010 A | 12/1998 | Wurzer et al. | | 6,197,023 B1 | 3/2001 | Muntermann |
| 5,853,409 A | 12/1998 | Swanson et al. | | 6,203,541 B1 | 3/2001 | Keppel |
| 5,860,832 A | 1/1999 | Wayt et al. | | 6,210,403 B1 | 4/2001 | Klicek |
| 5,865,788 A | 2/1999 | Edwards et al. | | 6,216,704 B1 | 4/2001 | Ingle et al. |
| 5,868,737 A * | 2/1999 | Taylor et al. .................... 606/34 | | 6,222,356 B1 | 4/2001 | Taghizadeh-Kaschani |
| 5,868,739 A | 2/1999 | Lindenmeier et al. | | 6,228,078 B1 | 5/2001 | Eggers et al. |
| 5,868,740 A | 2/1999 | LeVeen et al. | | 6,228,080 B1 | 5/2001 | Gines |
| 5,871,481 A | 2/1999 | Kannenberg et al. | | 6,228,081 B1 | 5/2001 | Goble |
| 5,891,142 A | 4/1999 | Eggers et al. | | 6,231,569 B1 | 5/2001 | Bek |
| 5,897,552 A | 4/1999 | Edwards et al. | | 6,232,556 B1 | 5/2001 | Daugherty et al. |
| 5,906,614 A | 5/1999 | Stern et al. | | 6,235,020 B1 | 5/2001 | Cheng et al. |
| 5,908,444 A | 6/1999 | Azure | | 6,235,022 B1 | 5/2001 | Hallock et al. |
| 5,913,882 A | 6/1999 | King | | 6,237,604 B1 | 5/2001 | Burnside et al. |
| 5,921,982 A | 7/1999 | Lesh et al. | | 6,238,387 B1 | 5/2001 | Miller, III |
| 5,925,070 A | 7/1999 | King et al. | | 6,238,388 B1 | 5/2001 | Ellman |
| 5,931,836 A | 8/1999 | Hatta et al. | | 6,241,723 B1 | 6/2001 | Heim et al. |
| 5,938,690 A | 8/1999 | Law et al. | | 6,241,725 B1 | 6/2001 | Cosman |
| 5,944,553 A | 8/1999 | Yasui et al. | | 6,243,654 B1 | 6/2001 | Johnson et al. |
| 5,948,007 A | 9/1999 | Starkebaum et al. | | 6,245,061 B1 | 6/2001 | Panescu et al. |
| 5,951,545 A | 9/1999 | Schilling et al. | | 6,245,063 B1 | 6/2001 | Uphoff |
| 5,951,546 A | 9/1999 | Lorentzen | | 6,245,065 B1 | 6/2001 | Panescu |
| 5,954,686 A | 9/1999 | Garito et al. | | 6,246,912 B1 | 6/2001 | Sluijter et al. |
| 5,954,717 A | 9/1999 | Behl et al. | | 6,251,106 B1 | 6/2001 | Becker et al. |
| 5,954,719 A | 9/1999 | Chen et al. | | 6,254,422 B1 | 7/2001 | Feye-Hohmann |
| 5,957,961 A | 9/1999 | Maguire et al. | | 6,258,085 B1 | 7/2001 | Eggleston |
| 5,959,253 A | 9/1999 | Shinchi | | 6,261,285 B1 | 7/2001 | Novak |
| 5,961,344 A | 10/1999 | Rosales et al. | | 6,261,286 B1 | 7/2001 | Goble et al. |
| 5,964,746 A | 10/1999 | McCary | | 6,267,760 B1 | 7/2001 | Swanson |
| 5,971,980 A | 10/1999 | Sherman | | 6,273,886 B1 | 8/2001 | Edwards |
| 5,971,981 A | 10/1999 | Hill et al. | | 6,275,786 B1 | 8/2001 | Daners |
| 5,976,128 A | 11/1999 | Schilling et al. | | 6,293,941 B1 | 9/2001 | Strul |
| 5,983,141 A | 11/1999 | Sluijter et al. | | 6,293,942 B1 * | 9/2001 | Goble et al. .................... 606/38 |
| 6,007,532 A | 12/1999 | Netherly | | 6,293,943 B1 | 9/2001 | Panescu et al. |
| 6,010,499 A | 1/2000 | Cobb | | 6,296,636 B1 | 10/2001 | Cheng et al. |
| 6,013,074 A | 1/2000 | Taylor | | 6,306,131 B1 | 10/2001 | Hareyama et al. |
| 6,014,581 A | 1/2000 | Whayne et al. | | 6,306,134 B1 | 10/2001 | Goble et al. |
| 6,017,338 A | 1/2000 | Brucker et al. | | 6,309,386 B1 | 10/2001 | Bek |

| Patent | Date | Inventor |
|---|---|---|
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Bloom et al. |
| 6,623,423 B2 | 9/2003 | Sakurai |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |

| Patent No. | Date | Inventors |
|---|---|---|
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Fleming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham et al. |
| 2005/0004569 A1 | 1/2005 | Witt et al. |
| 2005/0004634 A1 | 1/2005 | Ricart et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0109111 A1 | 5/2005 | Manlove et al. |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |

| | | | | | | |
|---|---|---|---|---|---|---|
| 2006/0291178 | A1 | 12/2006 | Shih | EP | 1293171 | 3/2003 |
| 2007/0038209 | A1 | 2/2007 | Buysse et al. | EP | 1472984 | 11/2004 |
| 2007/0093800 | A1 | 4/2007 | Wham et al. | EP | 1495712 | 1/2005 |
| 2007/0093801 | A1 | 4/2007 | Behnke | EP | 1500378 | 1/2005 |
| 2007/0135812 | A1 | 6/2007 | Sartor | EP | 1535581 | 6/2005 |
| 2007/0173802 | A1 | 7/2007 | Keppel | EP | 1609430 | 12/2005 |
| 2007/0173803 | A1 | 7/2007 | Wham et al. | EP | 1707144 | 3/2006 |
| 2007/0173804 | A1 | 7/2007 | Wham et al. | EP | 1645235 | 4/2006 |
| 2007/0173805 | A1 | 7/2007 | Weinberg et al. | EP | 880220 | 6/2006 |
| 2007/0173806 | A1 | 7/2007 | Orszulak et al. | EP | 1707143 | 10/2006 |
| 2007/0173810 | A1 | 7/2007 | Orszulak | EP | 1744354 | 1/2007 |
| 2007/0173813 | A1 | 7/2007 | Odom | EP | 1810628 | 7/2007 |
| 2007/0208339 | A1 | 9/2007 | Arts et al. | EP | 1810630 | 7/2007 |
| 2007/0225698 | A1 | 9/2007 | Orszulak et al. | EP | 1810633 | 7/2007 |
| 2007/0250052 | A1 | 10/2007 | Wham | EP | 1854423 | 11/2007 |
| 2007/0265612 | A1 | 11/2007 | Behnke et al. | FR | 1275415 | 10/1961 |
| 2007/0282320 | A1 | 12/2007 | Buysse et al. | FR | 1347865 | 11/1963 |
| 2008/0015563 | A1 | 1/2008 | Hoey et al. | FR | 2313708 | 12/1976 |
| 2008/0015564 | A1 | 1/2008 | Wham et al. | FR | 2364461 | 7/1978 |
| 2008/0039831 | A1 | 2/2008 | Odom et al. | FR | 2502935 | 10/1982 |
| 2008/0039836 | A1 | 2/2008 | Odom et al. | FR | 2517953 | 6/1983 |
| 2008/0082094 | A1 | 4/2008 | McPherson et al. | FR | 2573301 | 5/1986 |
| 2008/0125767 | A1 | 5/2008 | Blaha | GB | 607850 | 9/1948 |
| 2008/0177199 | A1 | 7/2008 | Podhajsky | GB | 702510 | 1/1954 |
| 2008/0248685 | A1 | 10/2008 | Sartor et al. | GB | 855459 | 11/1960 |
| 2008/0281315 | A1 | 11/2008 | Gines | GB | 902775 | 8/1962 |
| 2008/0281316 | A1 | 11/2008 | Carlton et al. | GB | 2164473 | 3/1986 |
| 2008/0287791 | A1 | 11/2008 | Orszulak et al. | GB | 2214430 | 9/1989 |
| 2008/0287838 | A1 | 11/2008 | Orszulak et al. | GB | 2358934 | 8/2001 |
| 2009/0018536 | A1 | 1/2009 | Behnke | SU | 166452 | 1/1965 |
| 2009/0024120 | A1 | 1/2009 | Sartor | SU | 727201 | 4/1980 |
| 2009/0036883 | A1 | 2/2009 | Behnke | WO | WO92/06642 | 4/1992 |
| 2009/0069801 | A1 | 3/2009 | Jensen et al. | WO | WO93/24066 | 12/1993 |
| 2009/0082765 | A1 | 3/2009 | Collins et al. | WO | WO94/24949 | 11/1994 |
| 2009/0157071 | A1 | 6/2009 | Wham et al. | WO | WO94/28809 | 12/1994 |
| 2009/0157072 | A1 | 6/2009 | Wham et al. | WO | WO95/09577 | 4/1995 |
| 2009/0157073 | A1 | 6/2009 | Orszulak | WO | WO95/19148 | 7/1995 |
| 2009/0157075 | A1 | 6/2009 | Wham et al. | WO | WO95/25471 | 9/1995 |

FOREIGN PATENT DOCUMENTS

| | | |
|---|---|---|
| WO | WO96/02180 | 2/1996 |
| WO | WO96/04860 | 2/1996 |
| DE | 1099658 | 2/1961 |
| WO | WO96/08794 | 3/1996 |
| DE | 1139927 | 11/1962 |
| WO | WO96/18349 | 6/1996 |
| DE | 1149832 | 6/1963 |
| WO | WO96/29946 | 10/1996 |
| DE | 1439302 | 1/1969 |
| WO | WO96/39086 | 12/1996 |
| DE | 2439587 | 2/1975 |
| WO | WO96/39914 | 12/1996 |
| DE | 2455174 | 5/1975 |
| WO | WO97/06739 | 2/1997 |
| DE | 2407559 | 8/1975 |
| WO | WO97/06740 | 2/1997 |
| DE | 2602517 | 7/1976 |
| WO | WO97/06855 | 2/1997 |
| DE | 2504280 | 8/1976 |
| WO | WO97/11648 | 4/1997 |
| DE | 2540968 | 3/1977 |
| WO | WO97/17029 | 5/1997 |
| DE | 2820908 | 11/1978 |
| WO | WO98/07378 | 2/1998 |
| DE | 2803275 | 8/1979 |
| WO | WO98/18395 | 5/1998 |
| DE | 2823291 | 11/1979 |
| WO | WO98/27880 | 7/1998 |
| DE | 2946728 | 5/1981 |
| WO | WO99/12607 | 3/1999 |
| DE | 3143421 | 5/1982 |
| WO | WO02/00129 | 1/2002 |
| DE | 3045996 | 7/1982 |
| WO | WO02/11634 | 2/2002 |
| DE | 3120102 | 12/1982 |
| WO | WO02/45589 | 6/2002 |
| DE | 3510586 | 10/1986 |
| WO | WO02/47565 | 6/2002 |
| DE | 3604823 | 8/1987 |
| WO | WO02/053048 | 7/2002 |
| DE | 390937 | 4/1989 |
| WO | WO02/088128 | 7/2002 |
| DE | 3904558 | 8/1990 |
| WO | WO03/090630 | 11/2003 |
| DE | 3942998 | 7/1991 |
| WO | WO03/090635 | 11/2003 |
| DE | 4339049 | 5/1995 |
| WO | WO03/092520 | 11/2003 |
| DE | 19717411 | 11/1998 |
| WO | WO2004/028385 | 4/2004 |
| DE | 19848540 | 5/2000 |
| WO | WO2004/098385 | 4/2004 |
| EP | 246350 | 11/1987 |
| WO | WO2004/043240 | 5/2004 |
| EP | 310431 | 4/1989 |
| WO | WO2004/052182 | 6/2004 |
| EP | 325456 | 7/1989 |
| WO | WO2004/103156 | 12/2004 |
| EP | 336742 | 10/1989 |
| WO | WO2005/046496 | 5/2005 |
| EP | 390937 | 10/1990 |
| WO | WO2005/048809 | 6/2005 |
| EP | 556705 | 8/1993 |
| WO | WO2005/050151 | 6/2005 |
| EP | 569130 | 11/1993 |
| WO | WO2005/060365 | 7/2005 |
| EP | 608609 | 8/1994 |
| WO | WO2005/060849 | 7/2005 |
| EP | 0694291 | 1/1996 |
| WO | WO2006/050888 | 5/2006 |
| EP | 836868 | 4/1998 |
| WO | WO2006/105121 | 10/2006 |
| EP | 878169 | 11/1998 |
| EP | 1051948 | 11/2000 |
| EP | 1053720 | 11/2000 |
| EP | 1151725 | 11/2001 |

OTHER PUBLICATIONS

International Search Report EP 07010673.7 dated Sep. 24, 2007.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William Rh, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
Ni W. et al. "A Signal Processing Method for the Coriolis Mass Flowmeter Based on a Normalized . . . ." Journal of Applied Sciences-Yingyong Kexue Xuebao, Shangha CN, vol. 23 No. 2;(Mar. 2005); pp. 160-164.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
Japanese Office Action dated Jun. 2, 2010 (Notice of Reasons for Rejection. pp. 1-4) regarding copending Japanese Appln. No. 2004-216626.
US 6,878,148, 04/2005, Goble et al. (withdrawn)

* cited by examiner

METHOD AND SYSTEM FOR CONTROLLING OUTPUT OF RF MEDICAL GENERATOR

CROSS REFERENCE TO RELATED APPLICATIONS

This application is a divisional application of U.S. application Ser. No. 10/427,832, filed May 1, 2003, by Wham et al., entitled "VESSEL SEALING SYSTEM", now U.S. Pat. No. 7,137,980, which is a continuation-in-part of U.S. application Ser. No. 10/073,761, filed on Feb. 11, 2002, by Wham et al., entitled "VESSEL SEALING SYSTEM", now U.S. Pat. No. 6,796,981, which is a continuation-in-part of U.S. Ser. No. 09/408,944, now U.S. Pat. No. 6,398,779, filed on Sep. 30, 1999 by Buysse et al., entitled "VESSEL SEALING SYSTEM", which claims the benefit of the priority date for provisional application No. 60/105,417, filed on Oct. 23, 1998, the entire contents of all of these applications are hereby incorporated by reference herein in their entirety.

BACKGROUND

The present invention is directed to electrosurgical surgery and, in particular, to a closed loop control system for an electrosurgical generator.

TECHNICAL FIELD

Electrosurgical generators are employed by surgeons in conjunction with an electrosurgical instrument to cut, coagulate, dessicate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electrodiathermy"). The term "coagulation" is defined as a process of desiccating tissue wherein the tissue cells are ruptured and dried. "Vessel sealing" is defined as the process of liquefying the collagen and elastin in the tissue so that it reforms into a fused mass with significantly-reduced demarcation between the opposing tissue structures (opposing walls of the lumen). Coagulation of small vessels is usually sufficient to permanently close them. Larger vessels or tissue need to be sealed to assure permanent closure.

In order to achieve one of the above desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

It is known that measuring the electrical impedance and change thereof across the tissue at the surgical site provides a good indication of the state of desiccation or drying of the tissue, e.g., as the tissue dries or looses moisture, the impedance across the tissue rises. This observation has been utilized in some electrosurgical generators to regulate the electrosurgical power based on a measurement of tissue impedance. For example, commonly owned U.S. Pat. No. 6,210,403 relates to a system and method for automatically measuring the tissue impedance and altering the output of the electrosurgical generator based on the measured impedance across the tissue. The entire contents of this patent is hereby incorporated by reference herein.

It has been determined that the particular waveform of electrosurgical energy can be tailored to enhance a desired surgical effect, e.g., cutting, coagulation, sealing, blend, etc. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. In order to effectively and consistently seal vessels or tissue, a pulse-like waveform is preferred. Energy may be supplied in a continuous fashion to seal vessels in tissue if the energy input/output is responsive to tissue hydration/volume through feedback control. Delivery of the electrosurgical energy in pulses allows the tissue to cool down and also allows some moisture to return to the tissue between pulses which are both known to enhance the sealing process.

It is further known to clamp or clip excess voltage output from the electrosurgical generator by the use of avalanche devices, such as diodes, zener diodes and transorbs, resulting in absorption and dissipation of excess energy in the form of heat.

Commonly owned U.S. Pat. No. 6,398,779 discloses a sensor which measures the initial tissue impedance with a calibrating pulse which, in turn, sets various electrical parameters based on a look-up table stored in a computer database. The transient pulse width associated with each pulse measured during activation is used to set the duty cycle and amplitude of the next pulse. Generation of electrosurgical power is automatically terminated based on a predetermined value of the tissue impedance across the tissue.

Thus a need exists to develop an electrosurgical generator having improved control circuitry and/or processing for providing continuous control of various electrical parameters (e.g., pulse frequency and intensity, voltage, current, power) of the electrosurgical generator based upon sensing information obtained from the surgical site relating to tissue impedance, changes in tissue impedance, tissue temperature, changes in tissue temperature, surgical intent (e.g., cutting, coagulating, sealing), tissue type, leakage current, applied voltage, applied current, tissue hydration levels, tissue compliance, and/or tissue optic transmission.

SUMMARY

A closed-loop control system is disclosed for use with an electrosurgical generator that generates electrosurgical energy. The closed loop control system includes a user interface for allowing a user to select at least one pre-surgical parameter, such as the type of surgical instrument operatively connected to the generator, the type of tissue and/or desired surgical effect. A sensor module is also included for continually sensing at least one of electrical and physical properties proximate a surgical site and generating at least one signal relating thereto. The closed loop control system also includes a control module for continually receiving the selected at least one pre-surgical parameter from the user interface and each of the signals from the sensor module, and processing each of the signals in accordance with the at least one pre-surgical parameter using a microprocessor, computer algorithm and/or a mapping (e.g., look-up table, continuous mapping and equivalent). The control module generates at least one corresponding control signal relating to each signal from the sensor module, and relays the control signal to the electrosurgical generator for controlling the generator.

A method is also disclosed for performing an electrosurgical procedure at a surgical site on a patient. The method includes the steps of applying at least one electrical pulse (pulsed or continuous) to the surgical site; continually sensing electrical and physical properties proximate the surgical site; and varying pulse parameters of the individual pulses of the at least one pulse in accordance with the continually-sensed properties.

In another embodiment, a control system is provided, which includes a sensor module for sensing at least one property associated with a surgical site prior to a surgical procedure (pre-surgical), during the surgical procedure and/or after the surgical procedure (post-surgical). The sensor module generates at least one signal relating to the property back to the control module. A control module which is executable on a processor receives each signal and processes the signals utilizing a computer algorithm and/or a mapping and generates one or more control signals relating thereto. The control signal is then communicated to the electrosurgical generator for controlling the generator.

BRIEF DESCRIPTION OF THE DRAWINGS

Various embodiments will be described herein below with reference to the drawings wherein.

DETAILED DESCRIPTION

Figure 1:
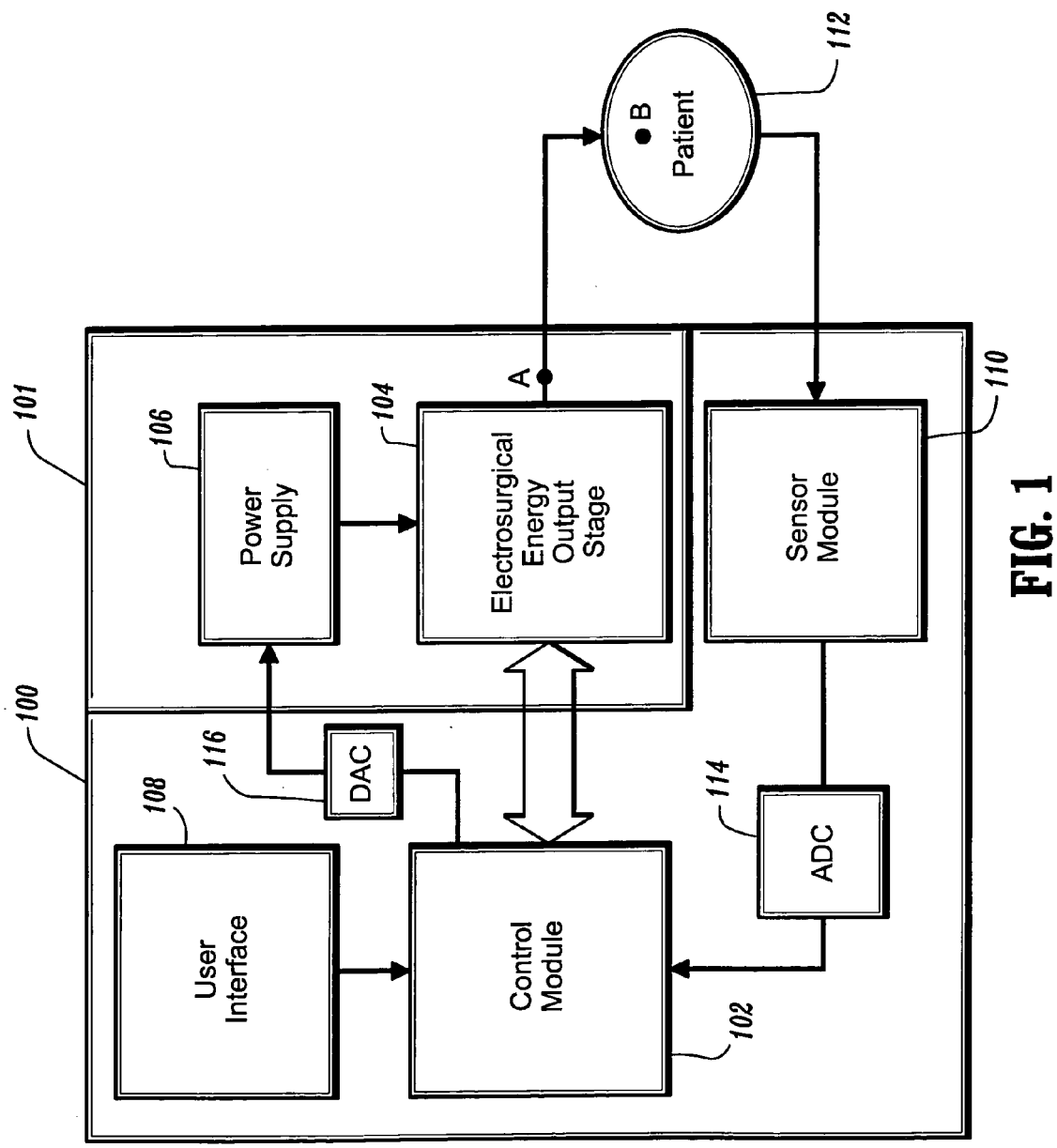
FIG. 1 is a schematic diagram of a closed-loop control system for use with an electrosurgical generator according to the present disclosure.

Reference should be made to the drawings where like reference numerals refer to similar elements throughout the various figures. Referring to FIG. 1, there is shown a schematic diagram of one embodiment of the presently disclosed closed loop control system 100 for use with an electrosurgical generator 101. Control system 100 includes a control module 102, user interface 108 and sensor module 110. The control module 102 is operatively connected to the electrosurgical generator 101. The electrosurgical generator 101 preferably includes electrosurgical energy output stage 104 and a power supply 106, where the output stage 104 receives power from the power supply 106 and delivers RF energy to a patient 112 via at least one electrode (not shown). As can be appreciated one or more electrodes may be used with the electrosurgical instrument for performing monopolar or bipolar surgery.

The sensor module 110 senses various electrical and physical parameters or properties at the operating site and communicates with the control module 102 to regulate the electrosurgical output from the output stage 104. It is envisioned that the sensor module 110 may be configured to measure or "sense" various electrical or electromechanical conditions at the operating site such as: tissue impedance, changes in tissue impedance, tissue temperature, changes in tissue temperature, leakage current, applied voltage and applied current. Preferably, the sensor module 110 measures one or more of these conditions continuously or in "real time" such that the control module 102 can continually modulate the electrosurgical output according to a specific purpose or desired surgical intent. More particularly, analog signals provided by the sensor module 110 are converted to digital signals via an analog-to-digital converter (ADC) 114, which in turn are provided to the control module 102.

The control module 102, thereafter, regulates the power supply 106 and/or the output stage 104 according to the information obtained from the sensor module 110. The user interface 108 is electrically connected to the control module 102 to allow the user to control various parameters of the electrosurgical energy output to the patient 114 during surgery to manually set, regulate and/or control one or more electrical parameters of the delivered RF energy, such as voltage, current, power, frequency, amplified, and/or pulse parameters, e.g., pulse width, duty cycle, crest factor, and/or repetition rate depending upon a particular purpose or to change surgical intent.

The control module 102 includes at least one microprocessor capable of executing software instructions for processing data received by the user interface 108 and the sensor module 110 for outputting control signals to the output stage 104 and/or the power supply 106, accordingly. The software instructions executable by the control module are stored in an internal memory in the control module 102, an internal or external memory bank accessible by the control module 102 and/or an external memory, e.g., an external hard drive, floppy diskette, CD-ROM, etc. Control signals from the control module 102 to the electrosurgical generator 101 may be converted to analog signals by a digital-to-analog converter (DAC) 116.

The power supply 106 is preferably a high voltage DC power supply for producing electrosurgical current, e.g., radiofrequency (RF) current. Signals received from the control module 102 control the magnitude of the voltage and current output by the DC power supply. The output stage 104 receives the output current from the DC power supply and generates one or more pulses via a waveform generator (not shown). As can be appreciated, the pulse parameters, such as pulse width, duty cycle, crest factor and repetition rate are regulated in response to the signals received from the control module 102. Alternatively, the power supply 106 may be an AC power supply, and the output stage 104 may vary the waveform of the signal received from power supply 106 to achieve a desired waveform.

As mentioned above, the user interface 108 may be local to or remote from the control module 102. A user may enter data such as the type of electrosurgical instrument being used, the type of electrosurgical procedure to be performed, and/or the tissue type upon which the electrosurgical procedure is being performed. It is envisioned that the closed loop control system 100, in particular the sensor module, may include one or more smart sensors which provide feedback to the surgeon relating to one or more of these physical parameters. Furthermore, the user may enter commands, such as a target effective voltage, current or power level to be maintained, or a target response e.g., change in regulation of the power supply 106 and/or output stage 104, to changes in sensed values, such as an effective change in voltage, current and/or power level as a function of the changes. Preferably, the user may also enter commands for controlling electrical parameters of the RF energy, delivered by the electrosurgical generator 101, as described above. It is envisioned that default values are provided for the above target levels and target responses.

The sensor module 110 includes a plurality of sensors (not shown) strategically located for sensing various properties or conditions at or proximate points "A" and "B". Sensors positioned at or proximate point "A" (hereinafter referred to as at point "A") sense properties and/or parameters of electrosurgical output from output stage 104, and/or properties, parameters or conditions prior to surgical effect of the currently administered electrosurgical energy during the surgical procedure. For example, sensors positioned at point "A" may be provided with or attached proximate the generator 101.

Sensors positioned at or proximate point "B" (hereinafter referred to as at point "B") sense parameters, properties and/or conditions at or across the operating site prior to the surgical procedure and/or in response to surgical effect during the surgical procedure. Preferably, one or more of these sensors may be included with the electrosurgical instrument, (e.g., on one end effector or opposing end effectors) or attached proximate the operating site. For example, optical sensors, proximity sensors, temperature sensors may be used to detect certain tissue characteristics, and electrical sensors may be employed to sense other parameters of the tissue or operating effects. It is noteworthy that point "A" may be located proximate the surgical site "B" at a location where the signals outputted by the generator 101 are propagated before they are applied or approximately when they are applied to the surgical site "B".

The sensors are provided with leads or wireless means for transmitting information to the control module, where the information is provided directly to the control module 102, and/or provided to the control module 102 via the sensor module 110 and/or the ADC 114. The sensor module 110 may include means for receiving information from multiple sensors, and providing the information and the source of the information (e.g., the particular sensor providing the information) to the control module 102.

Figure 2:
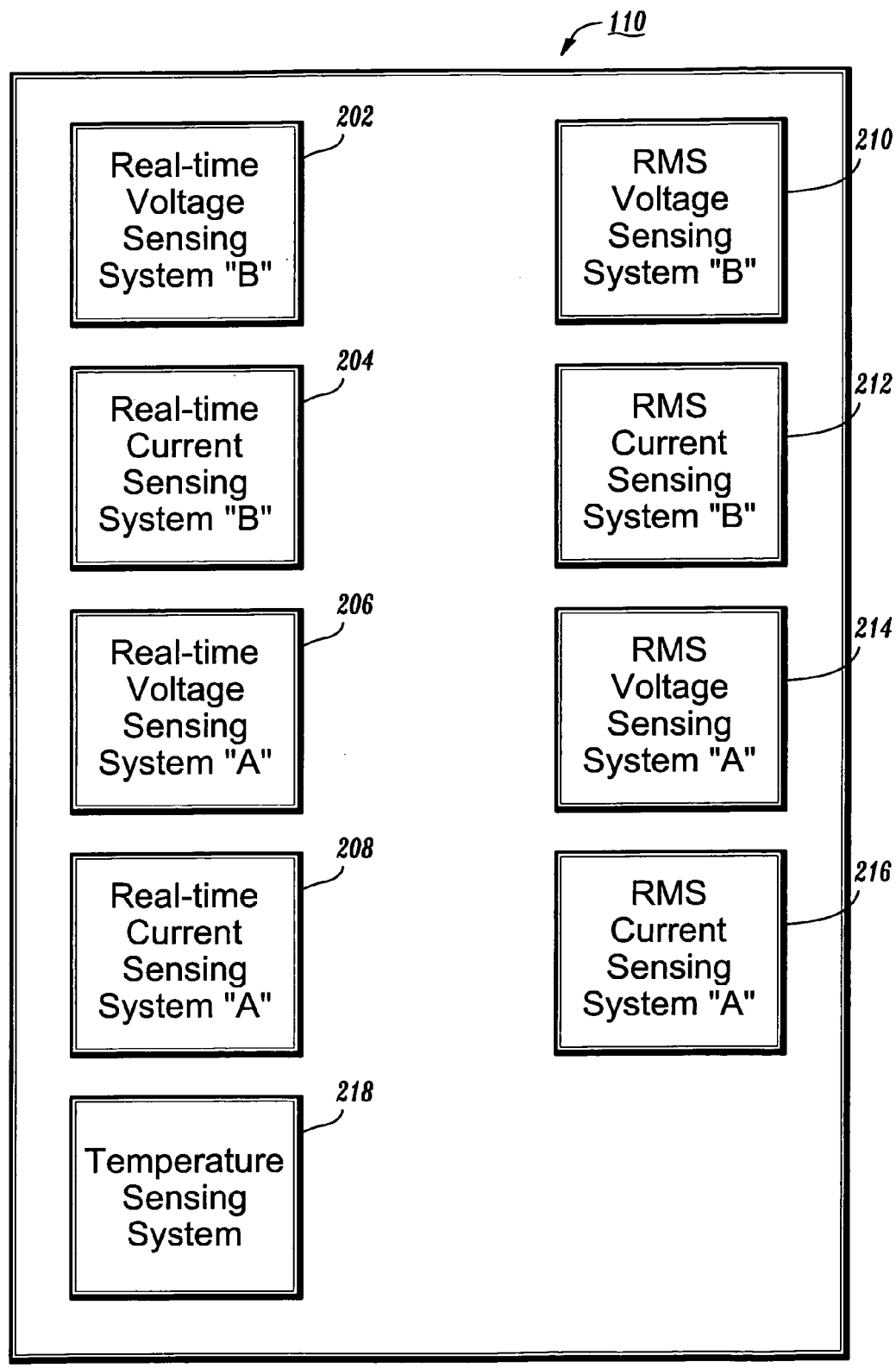
FIG. 2 is a schematic diagram of a sensor module for use with the closed-loop control system of FIG. 1.

With reference to FIG. 2, the inner-working components of the sensor module 110 are shown in greater detail. More particularly, the sensor module 110 preferably includes a real-time voltage sensing system 202 and a real-time current sensing system 204 for sensing real-time values for applied voltage and current at the surgical site "B". The sensor module 110 also preferably includes a real-time voltage sensing system 206 and a real-time current sensing system 208 for sensing real-time values of signals returned from the patent at a point "A". An RMS voltage sensing system 210 and an RMS current sensing system 212 are also included for sensing and deriving RMS values for applied voltage and current at the surgical site "B", and an RMS voltage sensing system 214 and an RMS current sensing system 216 are included for sensing and deriving RMS values of signals at point "A". A temperature sensing system 218 is preferably included for sensing tissue temperature at the surgical site "B". Real-time and RMS current and voltage sensing systems are known in the art. The sensor module 110 may further include sensors (not shown) for sensing voltage and current output by the generator.

The measured or sensed values are further processed, either by circuitry and/or a processor (not shown) in the sensor module 110 and/or by the control module 102, for deriving changes in sensed values and tissue impedance at the surgical site "B". Tissue impedance and changes in tissue impedance may be determined by measuring the voltage and/or current across the tissue and/or calculating changes thereof over time, and comparing the voltage and current values to known and/or desired values associated with various tissue types for use by the control system 100 to drive electrical output to achieve desired impedance and/or change in impedance values. As can be appreciated, these known and/or desired values, tissue types and ranges may be stored in an internal look-up table, "a continuous value map" or in an external searchable memory. Commonly owned U.S. Pat. Nos. 6,398,779, 6,203,541, 5,827,271 and U.S. application Ser. No. 10,073,761 disclose methods for measuring tissue impedance, and are incorporated by reference herein in their entirety.

It is envisioned that deriving tissue impedance (or other physical and electrical parameters) from real-time value(s) provides the benefit of monitoring real-time tissue impedance and/or changes in tissue impedance. As the surgical procedure proceeds, it is believed that the tissue impedance fluctuates in response to removal and restoration of liquids from the tissue at the surgical site "B". As the control module 102 monitors the tissue impedance and changes in tissue impedance (or other physical and electrical parameters) the control module 102 regulates the power supply 106 and output stage 104 accordingly for achieving the desired and optimal electrosurgical effect.

Before beginning an electrosurgical procedure, an operator of the electrosurgical instrument enters information via the user interface 108. Information entered includes, for example, the type of electrosurgical instrument being used, the type of procedure being performed (i.e., desired surgical effect), the type of tissue, relevant patient information, and a control mode setting. The control mode setting determines the amount of or type of control that the control module 102 will provide. As mentioned above, one or more sensors (not shown) may also be included to automatically provide information to the control module 102 relating to tissue type, initial tissue thickness, initial tissue impedance, etc.

Exemplary modes include, but are not limited to, one or a combination of one or more of the following modes: a first mode wherein the control module 102 maintains a steady selected output power, current and/or voltage value at site "A"; a second mode wherein the control module 102 maintains a steady selected output power, current and/or voltage value at site "B"; a third mode wherein the control module 102 maintains a variable selected output power, current and/or voltage values at site "A" which is dependent upon (i.e., a function of) time value(s) and/or sensed parameter(s) or changes in sensed parameter(s) during the procedure; a fourth mode wherein the control module 102 maintains a variable selected output power, current and/or voltage values at site "B", which is dependent upon (i.e., a function of) time value(s) and/or sensed parameter(s) or changes in sensed parameter(s) during the procedure. Functions performed on the time value(s) and sensed properties(s) include operations such as calculations and/or look-up operations using a table or map stored by or accessible by the control module 102. The control module 102 processes the selected output power, current and voltage values, such as by performing calculations or table look up operations, to determine power control signal values and output control values.

It is also envisioned that, the control module 102 determines initial settings for control signals to the power supply 106 and the output stage 104 by using and/or processing operator-entered data or settings, performing calculations and/ or accessing a look-up table stored by or accessible by the control module 102. Once the electrosurgical procedure begins, the sensors of sensor module 110 sense various physical and electrical properties and provide feedback to the control module 102 through the ADC 114 as needed. The control module 102 processes the feedback information in accordance with the pre selected mode, as well as any additional operator-entered commands entered during the procedure. The control module then sends control information to the power supply 106 and the output stage 104. It is contemplated that the generator 101 may be provided with override controls, to allow the operator to override the control signals provided by the control module 102, if needed, e.g., by entering override commands via the user interface 108.

Figure 3:
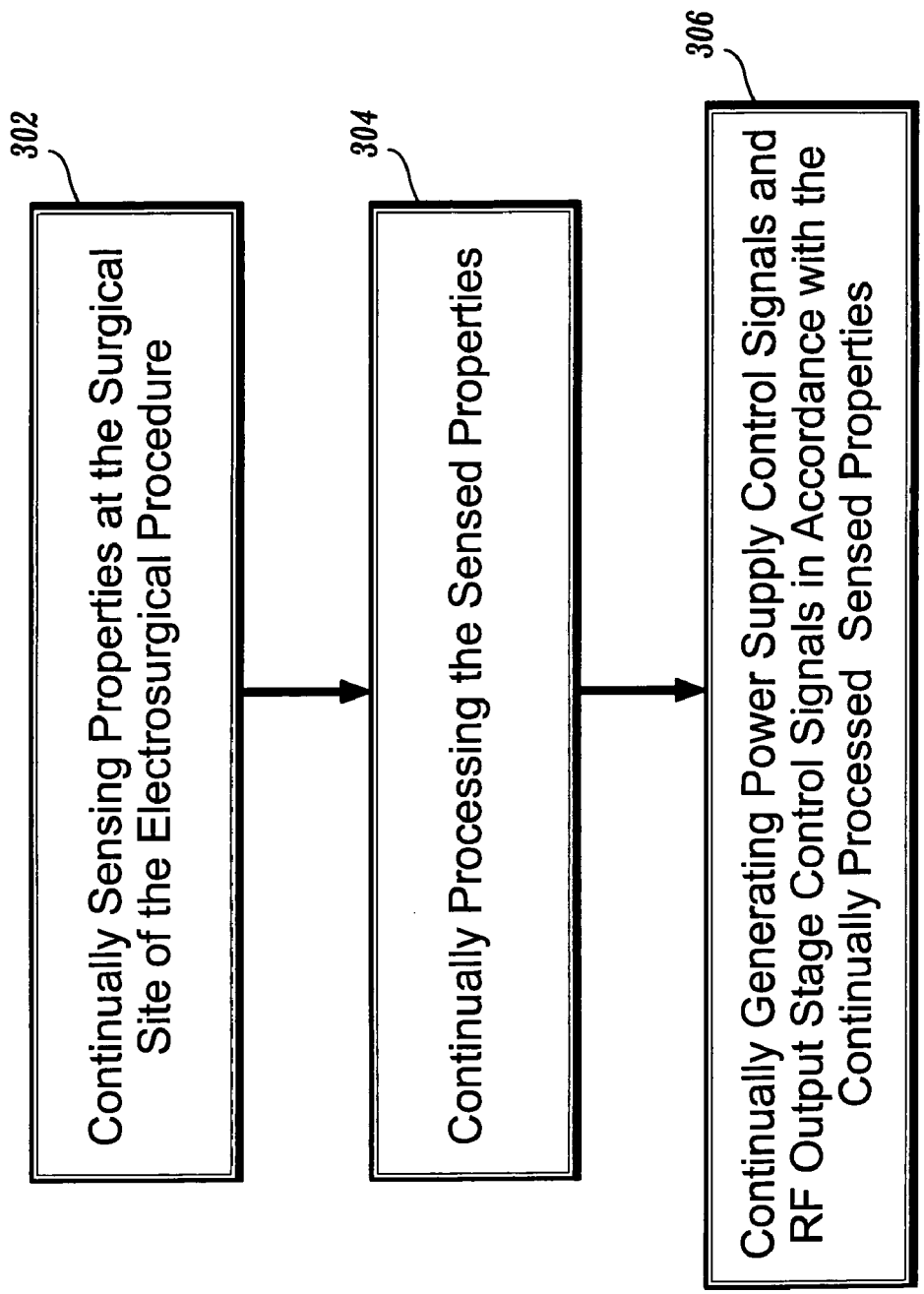
FIG. 3 is a flowchart illustrating a method of operation of the closed-loop control system according to the present disclosure.

FIG. 3 shows a flow chart illustrating a method for controlling operation of the closed loop control system 100 during an electrosurgical procedure in accordance with an embodiment of the present disclosure. At step 302, the method includes continually sensing various physical and electrical properties at the surgical site. At step 304, the sensed properties are continually processed. At step 306, power supply control signals are continually generated for controlling the magnitude of the signals output by the electrosurgical generator and output stage control signals are continually generated, for controlling pulse parameters of the output signals in accordance with the continually-processed sensed properties.

It is contemplated that the sensor module 110 further includes a proximity sensor for sensing (measuring) tissue thickness proximate the surgical site "B", and generating a tissue thickness value. An initial tissue thickness value may be provided to the control module 102 as a pre-surgical parameter. Sensed real time tissue thickness values and/or changes in tissue thickness values over time (Δ[difference] thickness/Δ[difference] time) may further be provided to the control module 102 during the surgical procedure, where the control module 102 modulates the electrical surgical output in accordance with the sensed real time tissue thickness values and/or changes in tissue thickness values over time.

It is further contemplated that the sensor module 110 further includes an additional sensor module (or the same sensor module 110 with additional capabilities) for sensing (measuring) tissue moisture (which is often indicative of tissue type) and generating a moisture content value and/or determining tissue type. It is envisioned that moisture content is determined from tissue compliance data or optical clarity. The additional sensor module may include an infrared or optical sensor for sensing (measuring) light or energy generated by a source, such as an infrared or other light source, which is transmitted through or reflected from the tissue, where the sensed value is indicative of tissue moisture content and/or tissue type of tissue proximate the surgical site "B". An initial tissue moisture content value and/or tissue type may be provided to the control module 102 as a pre-surgical parameter. Sensed real time moisture content values and/or changes in moisture content over time (Δ(difference) moisture content/Δ(difference) time) may further be provided to the control module 102 during the surgical procedure, where the control module 102 modulates the electrical surgical output in accordance with the sensed real time moisture content values and/or changes in moisture content values over time.

Accordingly, the present disclosure provides a closed loop control system 100 for providing continual control of the power supply 106 and the output stage 104 in response to "sensed" physical or electrical properties at the surgical site and/or proximate the output stage.

Figure 4:
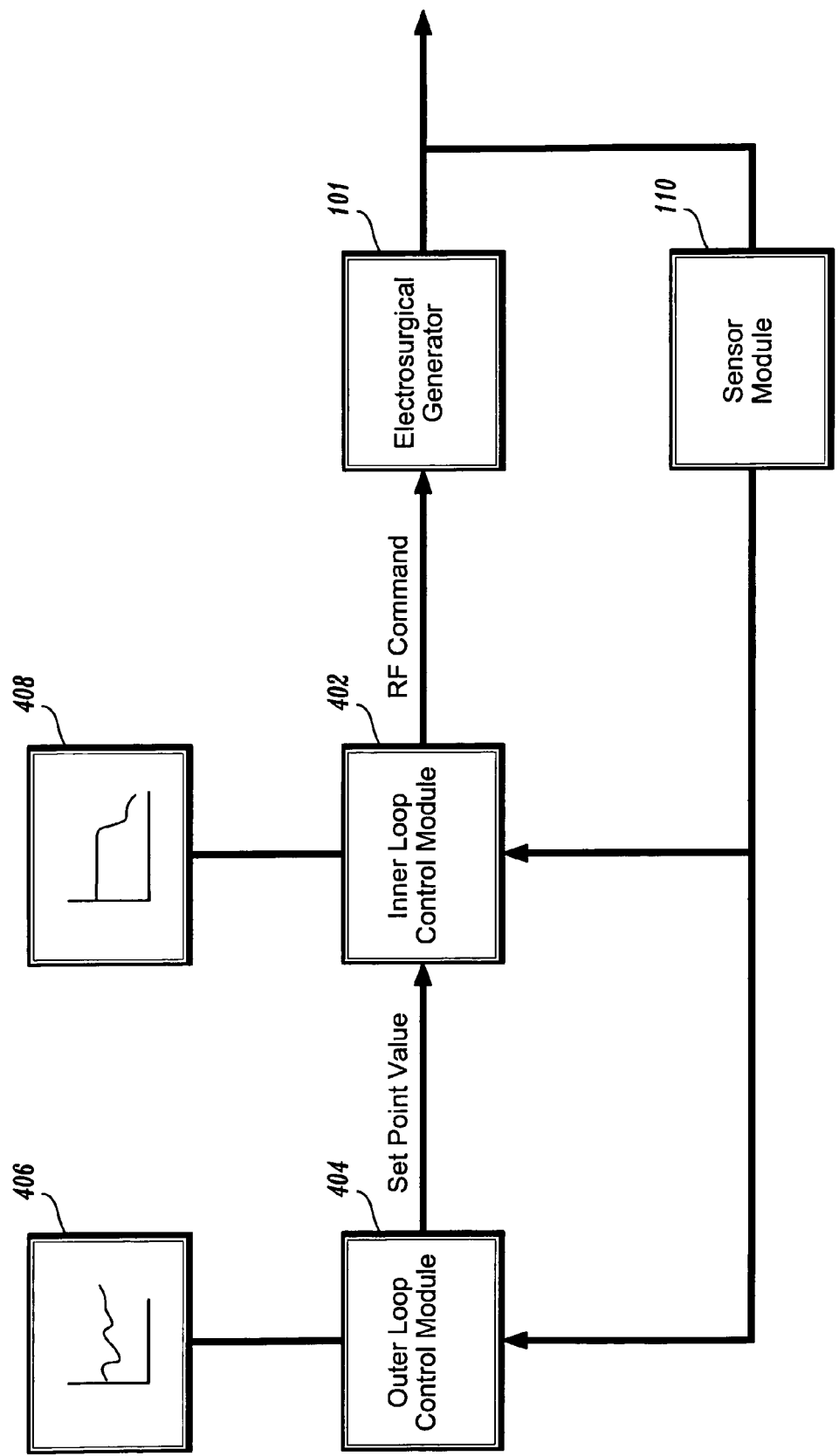
FIG. 4 is a block diagram of a dual loop control system in accordance with another embodiment of the invention.

In an additional embodiment according to the present disclosure and in particular reference to FIG. 4, the control module 102 is provided with two control loops, an inner loop controlled by inner loop control module 402 and an outer loop controlled by outer loop control module 404. Preferably, the inner and outer loop control modules 402, 404 are software modules executable by a processor of the control module 102.

The inner and outer loop control modules 402, 404 both receive signals generated by sensor module 110.

The inner loop control module 402 controls the amount of current, voltage and/or power delivered to the tissue for controlling a variable, e.g., I, V or P, sensed at the tissue and/or calculated from sensed values, until a desired event occurs (a rapid dz/dt or impedance rise is achieved), e.g., an impedance value is reached preferably in the range of about 200 ohms to about 400 ohms. The control variable is controlled to change during the course of the seal cycle according to impedance value (or other sensed and/or derived values), as determined by generator limitations (power, current, voltage) and surgical limitations (maximum limits for application of energy to tissue).

The inner loop control module 402 continually receives real time sensed values, such as current I and voltage V, from the sensor module 110 and may perform calculations on the received values for deriving additional real time values, such as power P and impedance Z. A desired inner loop value for I, V, and/or P are obtained by accessing at least one stored inner mapping of continuous values 408, look-up table or equivalent, where preferably the inner mapping 408 is in accordance with a function of impedance. Preferably, the inner loop control module 402 consults the inner mapping 408 for obtaining the desired inner loop value for the impedance currently being sensed and derived.

An algorithm is used to compare the real time value of I, V and/or P to the respective desired inner loop value and output an RF command to the electrosurgical generator 101 accordingly for achieving the desired inner loop value without exceeding the desired inner loop value, e.g., the RF command raises the target current, voltage and/or power output by the electrosurgical generator 101 when the real time value for I, V and/or P is lower than the respective desired inner loop value for I, V and/or P, and vice versa. It is contemplated that the RF command controls waveform parameters of electrosurgical energy output by the electrosurgical generator 101, including current, power, voltage, duty cycle, frequency, waveshape, etc. It is further contemplated that the inner loop is used without the outer loop for achieving the desired tissue effect.

The outer loop control module 404, layered over the inner loop control module 402, provides additional control of a variable for reaching a desired output value or effect. For example, control of the variable may monitor/regulate the rate of change of impedance of the tissue (sensed and calculated). In different embodiments, the variables controlled may include temperature, rate of change of temperature, and/or the energy input to the tissue. Outer loop control module 404 continually receives sensed values, such as I, V and temperature T from the sensor module 110 at a time "t" and performs calculations on the sensed values and preferably stored values for deriving values such as rate of change of impedance and/or rate of change in temperature. For example, the value for change in impedance (dz/dt) is obtained in accordance with:

$$dz/dt = (Z - Z\_OLD)/(t - t\_OLD); \qquad (1)$$

$$Z\_OLD = Z;$$

where Z is the impedance in accordance with values measured at time t; and

Z_OLD is the stored impedance in accordance with values measured at a previous time interval at time t_OLD An outer loop desired value for the control variable is obtained by accessing a stored outer mapping of continuous values 406, or alternatively a table or equivalent. The desired rate of change according to outer mapping 406 may be steady, or may depend on the stage of the seal cycle and change over time. The tissue is in a dynamic state during the seal procedure, and the outer loop monitors the rate of change throughout the procedure to determine the degree to which the desired rate of change is being achieved. When the control variable is temperature, a temperature map may be used for outer mapping 406 in which desired temperature is plotted versus time. When the control variable is rate of change in temperature, a rate of change in temperature map may be used for outer mapping 406 in which desired temperature is plotted versus time. Energy may be applied in a similar fashion, where an energy function can be calculated using equations derived for specific tissue types or using sensed values.

An algorithm is used to compare the real time sensed/calculated value of rate of change of impedance, temperature, rate of change of temperature and/or energy at time "t" to the respective desired outer value at time "t" obtained from the outer mapping 406 for determining if the desired outer value is met, and if not, for determining the ratio of the difference between the real time value and the desired outer value to the desired outer value. If the desired outer value is not being met, the outer loop module 406 generates a set point value which is provided to the inner loop module 402. The set point value is raised when the real time value for rate of change of impedance, temperature and/or rate of change of temperature is lower than the respective desired outer value for rate of change of impedance, temperature and/or rate of change of temperature, and vice versa.

The set point value is preferably a ratio signal for altering the inner mapping 408 by raising or lowering a plotted curve of the inner mapping 408 along the y-axis. Preferably, the ratio signal is a proportional integral derivative (PID) control signal, as is known in the art. The inner loop control module 402 responds instantaneously by accessing the altered inner mapping 408 for obtaining a desired inner value from the outer loop, comparing the real time value of the control variable, generating an RF command for achieving the desired inner value without exceeding the desired inner value, and outputting the RF command accordingly to the electrosurgical generator 101 for controlling voltage, current and/or power needed for achieving a desired tissue effect.

Preferably the outer loop control module 404 uses the real time value of rate of change of impedance, temperature, rate of change of temperature, and/or total energy delivered to determine if a desired outer value has been reached which indicates completion of a seal. Upon determination of seal completion, a stop signal is generated for stopping the sealing process. Otherwise, the outer loop continues to monitor, receive and process sensed values from the senor module 110.

Control of I, V and/or P by the inner loop control module 402 improves system stability and control capabilities in low impedance ranges, e.g., 0-20 ohms, which are critical for seal initiation, particularly by avoiding a low-end impedance break point which induces oscillation and lack of system control. The outer loop control enhances the control module's ability to control sealing in accordance with desired trends or events, to change seal intensity by changing the rate of change of impedance, and to enhance uniform sealing of tissue, i.e., normalize tissue in terms of variability, including tissue hydration, volume and composition. With feedback control and continuous sensing of the tissue's condition, there is not a need to switch control variables (i.e., low/high end break points), which improves system stability as explained above.

It is contemplated that the control module 102 controls a module for producing resistive heat for regulating heat applied to the tissue for achieving the desired tissue effect instead of or in addition to controlling the electrosurgical output stage 104 and/or the power supply 106. The control module 102 responds to sensed tissue temperature or other sensed properties indicative of tissue temperature, accesses at least one mapping, data table or equivalent using the sensed values for obtaining desired output current or resistivity values, and outputs a command signal for controlling output heat resistivity. Preferably, the module for producing resistive heat includes a current source and/or a variable resistor which are responsive to the command signal for outputting a desired current or providing a desired resistance, respectively.

It is envisioned that in another embodiment of the invention the control system includes a sensor module for sensing at least one property associated with a surgical site during at least one of a pre-surgical time prior to a surgical procedure, the surgical procedure and a post-surgical time following the surgical procedure for generating at least one signal relating thereto; and a control module executable on a processor for receiving said at least one signal and processing each of said signals using at least one of a computer algorithm and a mapping and generating at least one control signal in accordance with the processing, and providing the at least one control signal to the electrosurgical generator for controlling the generator. Preferably, the processing includes determining tissue type of tissue proximate the surgical site.

In an additional preferred embodiment, the sensor module 110 (or an additional sensor module (not shown)) senses at least one property as a pre-surgical condition, as a concurrent surgical condition and/or as a post-surgical condition. Preferably, the sensor module 110 senses at least two surgical conditions (or changes in surgical conditions over time) selected from pre-surgical, concurrent surgical and post-surgical conditions. Pre-surgical conditions include: degree of opaqueness of tissue proximate the surgical site; moisture content level of the tissue; and/or thickness of the tissue. Concurrent conditions include: degree of opaqueness of the tissue proximate the surgical site; moisture content level of the tissue; thickness of the tissue; temperature of the tissue; impedance of the tissue; current across the tissue; voltage across the tissue; power across the tissue; changes in degree of opaqueness of the tissue; changes in moisture content level of the tissue; changes in thickness of the tissue; changes in temperature of the tissue; changes in impedance of the tissue; changes in current across the tissue; changes in voltage across the tissue; and changes in power across the tissue. The post-surgical conditions include: degree of opaqueness of tissue; proximate the surgical site; moisture content level of the tissue; thickness of the tissue: temperature of the tissue; and impedance of the tissue.

Preferably, at least one property sensed during the post-surgical condition is indicative of the quality of a tissue seal formed during the surgical procedure. In a preferred embodiment the sensor module 110 includes a light detector for detecting light generated by a light source and transmitted through (or reflected from) the tissue proximate the surgical site. A proximity sensor having sensing elements placed at opposite surfaces of the tissue may also be included for sensing the distance between the elements which is indicative of the tissue thickness.

Although this disclosure has been described with respect to preferred embodiments, it will be readily apparent to those having ordinary skill in the art to which it appertains that changes and modifications may be made thereto without departing from the spirit or scope of the disclosure. For example, it is contemplated that the control module 102 may include circuitry and other hardware, rather than, or in combination with, programmable instructions executed by a microprocessor for processing the sensed values and determining the control signals to be sent to the power supply 106 and the output stage 104.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. An electrosurgical system comprising:
    an electrosurgical generator adapted to supply electrosurgical energy to tissue;
    a microprocessor configured to generate a target impedance trajectory having at least one slope, wherein the target impedance trajectory includes a plurality of target impedance values, the microprocessor also configured to drive tissue impedance along the target impedance trajectory by adjusting the output level to substantially match tissue impedance to a corresponding target impedance value, the microprocessor further configured to compare tissue impedance to a threshold impedance value and adjust output of the electrosurgical generator when the tissue impedance is equal to or greater than the threshold impedance; and
    an electrosurgical instrument including at least one active electrode adapted to apply electrosurgical energy to tissue, such that the tissue impedance is monitored in real-time in one or more closed loop control configurations by at least one control module that regulates the electrosurgical energy received from the generator, the one or more closed loop control configurations being an inner control loop configuration for controlling a first set of variables, the first set of variables selectively used to derive a second set of variables and an outer control loop configuration for providing additional control of a subset of at least one of the first and second sets of variables of the inner control loop.

2. An electrosurgical system as in claim 1, wherein the microprocessor is further configured to generate the threshold impedance value as a function of an offset impedance value and an ending impedance value.

3. An electrosurgical system as in claim 2, wherein the offset impedance value is selected from the group consisting of an impedance value corresponding to maximum current value, a minimum impedance value and an initial impedance value.

4. An electrosurgical system as in claim 1, wherein the microprocessor is further configured to compare duration of a reaction period to a reaction timer value and adjust output of the electrosurgical generator when the duration of the reaction period is equal to or greater than the reaction timer value.

5. An electrosurgical system as in claim 4, wherein the microprocessor is further configured to compare duration of the reaction period to a sum of the reaction timer value and a time offset period and adjust output of the electrosurgical generator when the duration of the reaction period is equal to or greater than the sum of the reaction timer value and the time offset period.

6. A method for performing an electrosurgical procedure comprising the steps of:
    applying electrosurgical energy at an output level to tissue from an electrosurgical generator;
    generating a target impedance trajectory, wherein the target impedance trajectory includes a plurality of target impedance values;
    driving tissue impedance along the target impedance trajectory by adjusting the output level to match tissue impedance to a corresponding target impedance value; and
    comparing tissue impedance to a threshold impedance value and adjusting output of the electrosurgical generator when the tissue impedance is equal to or greater than the threshold impedance, such that the tissue impedance is monitored in real-time in one or more closed loop control configurations by at least one control module that regulates the electrosurgical energy received from the generator, the one or more closed loop control configurations being an inner control loop configuration for controlling a first set of variables, the first set of variables selectively used to derive a second set of variables and an outer control loop configuration for providing additional control of a subset of at least one of the first and second sets of variables of the inner control loop.

7. A method as in claim 6, further comprising the step of generating the threshold impedance value as a function of an offset impedance value and an ending impedance value.

8. A method as in claim 7, wherein the step of generating the threshold impedance value further includes the step of selecting the offset impedance value from the group consisting of an impedance value corresponding to maximum current value, a minimum impedance value and an initial impedance value.

9. A method as in claim 6, further comprising the step of comparing duration of a reaction period to a reaction timer value and adjusting the output of the electrosurgical generator when the duration of the reaction period is equal to or greater than the reaction timer value.

10. A method as in claim 9, wherein the step of comparing duration of a reaction period further includes the step of comparing duration of the reaction period to a sum of the reaction timer value and a time offset period and adjusting the output of the electrosurgical generator when the duration of the reaction period is equal to or greater than the sum of the reaction timer value and the time offset period.

11. A method according to claim 6, wherein the step of generating the target impedance trajectory further includes the step of:
    generating a positively sloping impedance trajectory.

12. A method according to claim 6, wherein the step of generating the target impedance trajectory further includes the step of:
    generating a negatively sloping impedance trajectory.

13. A method according to claim 6, wherein the step of generating a target impedance trajectory further includes the step of:
    generating the slope of the target impedance trajectory to be at least one of a linear, quasi-linear, and non-linear trajectory.

14. An electrosurgical generator comprising:
    an RF output stage adapted to supply electrosurgical energy to tissue; and
    a microprocessor configured to generate a target impedance trajectory having at least one slope, wherein the target impedance trajectory includes a plurality of target impedance values, the microprocessor also configured to drive tissue impedance along the target impedance trajectory by adjusting the output level to substantially match tissue impedance to a corresponding target impedance value, the microprocessor further configured to compare tissue impedance to a threshold impedance value and adjust output of the electrosurgical generator when the tissue impedance is equal to or greater than the threshold impedance, such that the tissue impedance is monitored in real-time in one or more closed loop control configurations by at least one control module that regulates the electrosurgical energy received from the generator, the one or more closed loop control configurations being an inner control loop configuration for controlling a first set of variables, the first set of variables selectively used to derive a second set of variables and an outer control loop configuration for providing additional control of a subset of at least one of the first and second sets of variables of the inner control loop.

15. An electrosurgical generator as in claim 14, wherein the microprocessor is further configured to generate the threshold impedance value as a function of an offset impedance value and an ending impedance value.

16. An electrosurgical generator as in claim 15, wherein the offset impedance value is selected from the group consisting of an impedance value corresponding to maximum current value, a minimum impedance value and an initial impedance value.

17. An electrosurgical generator as in claim 14, wherein the microprocessor is further configured to compare duration of a reaction period to a reaction timer value and adjust output of the electrosurgical generator when the duration of the reaction period is equal to or greater than the reaction timer value.

18. An electrosurgical generator as in claim 17, wherein the microprocessor is further configured to compare duration of the reaction period to a sum of the reaction timer value and a time offset period and adjust output of the electrosurgical generator when the duration of the reaction period is equal to or greater than the sum of the reaction timer value and the time offset period.

\* \* \* \* \*